United States Patent [19]

Prisbylla

[11] Patent Number: 4,472,189

[45] Date of Patent: Sep. 18, 1984

[54] STANNIC N-PHOSPHONOMETHYGLYCINE AND ITS USE AS A HERBICIDE

[75] Inventor: Michael P. Prisbylla, Richmond, Calif.

[73] Assignee: Stauffer Chemical Co., Westport, Conn.

[21] Appl. No.: 453,557

[22] Filed: Dec. 27, 1982

[51] Int. Cl.³ .................... E05B 65/46; C07F 7/22
[52] U.S. Cl. ................................ 71/86; 260/429.7; 260/502.5 F
[58] Field of Search .................... 260/429.7, 502.5; 71/86

[56] References Cited

U.S. PATENT DOCUMENTS

| | | | |
|---|---|---|---|
| 3,442,922 | 5/1969 | Langer et al. | 260/429.7 |
| 3,556,762 | 1/1971 | Hamm | 71/86 |
| 3,799,758 | 3/1974 | Franz | 71/86 |
| 3,835,000 | 9/1974 | Frazier et al. | 204/78 |
| 3,853,530 | 10/1974 | Franz | 71/86 |
| 3,929,450 | 3/1976 | Hamm et al. | 71/86 |
| 3,977,860 | 8/1976 | Franz | 71/86 |
| 3,988,142 | 10/1976 | Franz | 71/86 |
| 4,140,513 | 2/1979 | Prill | 260/502.5 F |
| 4,147,719 | 4/1979 | Franz | 260/501.12 |
| 4,148,624 | 4/1979 | Maier | 71/86 |
| 4,206,156 | 6/1980 | Kamiya et al. | 260/502.5 R |
| 4,315,765 | 2/1982 | Large | 260/502.5 F |

*Primary Examiner*—Helen M. Sneed
*Attorney, Agent, or Firm*—Harry A. Pacini

[57] ABSTRACT

A herbicidal composition comprising stannic N-phosphonomethylglycine having a ratio of stannic (IV) cation to N-phosphonomethylglycine anion is from about 1:1 to about 1:6, and their use as herbicides.

9 Claims, No Drawings

STANNIC N-PHOSPHONOMETHYGLYCINE AND ITS USE AS A HERBICIDE

BACKGROUND OF THE INVENTION

This invention is directed to novel chemical compounds and their use in controlling weeds and regulating the natural growth or development of plants.

It is known that various features of plant growth can be modified or regulated to produce a variety of beneficial effects. For instance, plants can be defoliated and leaf growth inhibited while the productive plant parts remain unaffected. Such action often stimulates extra growth on the productive plant parts and facilitates harvesting operations. Chemical agents producing these effects are particularly useful in flax, cotton, and bean crops, and other crops of a similar nature. While defoliation results in the killing of leaves, it is not a herbicidal action since it does not harm the remainder of the plant. Indeed, killing of the treated plant is undesirable when defoliation is sought, since leaves will continue to adhere to a dead plant.

Another response demonstrated by plant growth regulants is the general retardation of vegetative growth. This response has a wide variety of beneficial features. In certain plants it causes a diminution or elimination of the normal apical dominance, leading to a shorter main stem and increased lateral branching. Smaller, bushier plants with increased resistance to drought and pest infestation are the result. Retardation of vegetative growth is also useful in turf grasses for lessening the vertical growth rate, enhancing root development, and producing a denser, sturdier turf. The retardation of turf grasses also serves to increase the interval between mowings of lawns, golf courses and similar grassy areas.

BRIEF DESCRIPTION OF THE INVENTION

It has now been discovered that stannic N-phosphonomethylglycine compounds are useful in regulating the natural growth or development to plants and to be phytotoxic to the plants. Accordingly, the invention relates to a method of controlling undesirable vegetation, comprising applying to the vegetation in postemergent state a herbicidally effective amount of the compounds. Herbicidal effects are generally achieved with a higher application rate than plant growth regulant effects. The compound is particularly effective in controlling grass weeds. The term "herbicidally effective amount" designates any amount which will kill a plant or any portion thereof. The term "plants" is intended to include germinant seeds, emerging seedlings, and established vegetation, including both roots and aboveground portions.

DETAILED DESCRIPTION OF THE INVENTION

Herbicidal effects are achieved by adversely affecting natural growth or development of plants, and the strength of the application can be varied to achieve the desired result. The compound of the instant invention serves to regulate the natural growth or development of treated plants in a number of diverse ways, and it should be understood that the regulatory effects will vary from one plant species to the next or from one application rate to the next.

The compounds of this invention are readily prepared from N-phosphonomethylglycine by reacting the latter with stannic oxide or stannic acetate in the presence of water to form an aqueous solution. The reactants in the reaction mixture are heated for a predetermined time at reflux temperature and then allowed to cool, filtered and the aqueous solution is concentrated to give the final product. When using this procedure for forming the compound of this invention, it has been found that the ratio of stannic (IV) cation to N-phosphonomethylglycine anion ratio is from about 1:1 to about 1:6.

The source of stannic cation can be from any form of tin which is in the four (IV) valence state, such as stannic oxides, stannic hydroxides, stannic acetate, and stannic chloride, which are commercially available. N-Phosphonomethylglycine is a readily available material that can be prepared by the phosphonomethylation of glycine, by reaction of ethyl glycinate with formaldehyde and diethylphosphite, or the oxidation of the N-phosphinomethylglycine. Such methods are described in U.S. Pat. No. 3,799,758 (Franz, March 1974) and U.S. Pat. No. 3,160,632 (Toy, December 1964).

Examples 1 and 2 illustrate the preparation of the compounds and Example 3 illustrates the non-selective herbicidal activity. These examples are merely illustrative, non-limiting demonstrations of the preparation of the compound of the present invention and of its effectiveness in controlling undesirable vegetation.

EXAMPLE 1

Preparation of Hydroxy Stannic Tris-N-Phosphonomethylglycine

Stannic (IV) oxide (1.508 g, 0.010 mole) was combined with 5.072 g (0.030 mole) of N-phosphonomethylglycine in a 200 milliliter flask containing 60 ml of deionized water. The flask was equipped with a magnetic stirrer. This solution was heated at reflux temperature for three hours, cooled and allowed to stir overnight at room temperature. The material was then filtered. The filter cake was washed with 30 ml deionized water, followed by 20 mlg of methanol, then 30 ml diethylether. The filter cake was dired in an oven. There was obtained 5.55 g of white powder with a m.p. >310° C. The white powder was subjected to standard anayltical procedures and the title compound as the dihydrate was confirmed with one part stannic and three parts if the N-phosphonomethylglycine anion. Analysis—Calculated $C_9H_{26}N_3P_3O_{18}Sn$: C 15.98%, H 3.85%, N 6.21%, P 13.76%, Sn 17.56%. Found: C 16.21%, H 3.61%, N 6.22%, P 13.60%, Sn 15.20%.

Also obtained from the filtrate at 45° C., <1 mm Hg, the methanol and ether washes, and aqueous filtrate and water washes, was 0.8 g white powder, which decomposed 218°–222° C.

EXAMPLE 2

Preparation of Stannic Tetra-N-Phosphonomethylglycine

Stannic oxide (1.5070 g, 0.010 mole) was combined with 6.762 g (0.040 mole) of N-phosphonomethylglycine in a 200 milliliters (ml) flask containing 60 ml of deionized water. The flask was equipped with a magnetic stirrer. This solution was heated at reflux temperature for three (3) hours, cooled and then allowed to stir overnight at 25° C. The material was then filtered to remove the solids and the aqueous filtrate. The filter cake was washed with two 20 ml portions of deionized water, followed with 20 ml methanol and 20 ml diethyl ehter. The filter cake was dried in an oven. There was obtained 7.1 g of white poweder, m.p. >310° C. The residue was 0.80 g of a white powder which was water-soluble, having a melting point of 231° C. The white powder was subjected to standard analytical procedures and the subject compound as the trihydrate was confirmed with one part stannic and four parts of the N-phosphonomethylglycine anion. Analysis—Calculated $C_{12}H_{34}N_4P_4O_{23}Sn$: C 17.04%, H 4.02%, N 6.62%, P 14.62%, Sn 14.0%. Found: C 17.11%, H 3.755, N 6.62%, P 14.56%, Sn 12.5%.

Also obtained from the filtrate after stripping at 45° C., 1 mm Hg, the methanol and ether washes and aqueous washes, a yield of 1.1 g of white solid m.p. decomp. 224° C.

EXAMPLE 3

Herbicidal Activity

This example demonstrates the herbicidal activity of the subject compounds.

Fiber planting flats measuring 15.2×25.4×7.0 cm were filled to a depth of 5.0 cm with loamy sand soil, containing 50 parts per million (ppm) each of the commercial fungicide cis-N[(trichloromethyl)thio]-4-cyclohexene-1,2-dicarboximide (Captan) and 17-17-17 fertilizer (percentages of N-$P_2O_5$-$K_2O$ on a weight basis). Several rows were impressed across the width of each flat and a variety of seeds of both grass and broadleaf plant species were planted. The weed species used are listed below:

| Grasses: | |
|---|---|
| WG | watergrass |
| WO | wild oats |
| FT | foxtail |
| Broadleaf Weeds: | |
| AMG | annual morning glory |
| VL | velvetleaf |
| MD | mustard |
| PW | pigweed |
| CD | curly dock |
| Other | |
| YNG | yellow nutsedge |

The broad leaf species and the grasses were seeded all on the same day. Ample seeds of each species were planted to produce 20 to 50 seedlings per row after emergence, depending on the size of each plant.

In the pre-emergence test the seeded flats were sprayed one day after treatment. In the post-emergence test, ten days after seeding, the emerged seedlings of all species were sprayed with aqueous solutions of the test compounds.

Stock solutin was prepared as follows. an initial solution opf 60 milliligrams (mg) in 45 ml of water was prpared for each compound. To an 18 ml aliquot was added 22 ml water and Tween®20 (surfactant), enough so that the final solution is 40 ml and contains 0.5% Tween®20 (polyoxyethylene sorbitan monolaurate) (v/v). Additional untreated flats were used as standards for measuring the extent of weed control in the treated flats. All flats were placed in greenhouses at 75°–80° F. and watered regularly.

Twelve days after treatment, the test flats were compared to the standards and the weeds in each row were rated visually in terms of percent control ranging from 0% to 100%, with 0% representing the same degree of growth as the same row in the standard and 100% representing complete kill of all weeds in the row. All types of plant injury were taken into consideration. The results are shown in Table I.

TABLE I

| Compound Number | Postemergence Herbicide Screen at 4 lb/A; 12 days after treatment | | | | | | | | | |
|---|---|---|---|---|---|---|---|---|---|---|
| | Weed Species | | | | | | | | Average | |
| | FT | WG | WO | AMG | VL | MD | CD | YNG | GRASSES | BROADLEAF |
| 1 | 100 | 100 | 90 | 50 | 60 | 100 | 50 | 60 | 97 | 65 |
| 2 | 100 | 100 | 95 | 65 | 70 | 100 | 85 | 40 | 98 | 80 |

TABLE II

| Compound Number | Preemergence Herbicide Screen at 4 lb/A; 12 days after treatment | | | | | | | | | |
|---|---|---|---|---|---|---|---|---|---|---|
| | FT | WG | WO | AMG | VL | MD | CD | YNS | Average | |
| | | | | | | | | | GRASSES | BROADLEAF |
| 1 | 0 | 0 | 0 | 0 | 0 | 0 | 0 | 0 | 0 | 0 |
| 2 | 0 | 0 | 0 | 0 | 0 | 0 | 0 | 0 | 0 | 0 |

METHODS OF APPLICATION

Whether it is used as a plant growth regulator or as a herbicide, the compound of the present invention is most useful when applied directly to the plants after their emergence from the soil. For application at a field site, the compound is generally embodied in a suitable formulation containing additional ingredients and diluent carriers to aid in its dispersal. Examples of such ingredients or carriers are water, organic solvents, dusts, granules, surface active agents, water-in-oil and oil-in-water emulsions, wetting agents, dispersing agents, and emulsifiers. The formulation generally takes the form of a dust, solution, emulsifiable concentrate, or wettable powder.

A. Dusts

Dusts are dense powder compositions which combine the active compounds with a dense, free-flowing solid carrier. They are intended for application in dry form and are designed to settle rapidly to avoid being windborne to areas where their presence is not desired.

The carrier may be of mineral or vegetable origin, and is preferably an organic or inorganic powder of high bulk density, low surface area, and low liquid absorptivity. Suitable carriers include micaceous talcs, pyrophyllite, dense kaolin clays, tobacco dust, and ground calcium phosphate rock.

The performance of a dust is sometimes aided by the inclusion of a liquid or solid wetting agent, of ionic, anionic, or nonionic character. Preferred wetting agents include alkylbenzene and alkylnaphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, and ditertiary acetylenic glycols. Dispersants are also useful in the same dust compositions. Typical dispersants include methyl cellulose, polyvinyl alcohol, lignin sulfonates, polymeric alkylnaphthalene sulfonates, sodium naphthalene sulfonate, polymethylene bisnaphthalenesulfonate, and sodium-N-methyl-N-(long chain acid) taurates.

In addition, inert absorptive grinding aids are frequently included in dust compositions to aid in the manufacturing of the dust. Suitable grinding aids include attapulgite clay, diatomaceous silica, synthetic fine silica and synthetic calcium and magnesium silicates.

In typical dust compositions, carriers are usually present in concentrations of from about 30 to 90 weight percent of the total composition. The grinding aid usually constitutes about 5 to 50 weight percent, and the wetting agent up to about 1.0 weight percent. Dispersants, when present, constitute up to about 0.5 weight percent, and minor amounts of anticaking and antistatic agents may also be present. The particle size of the entire composition is usually about 30 to 50 microns.

B. Solutions

Aqueous solutions of the active compounds are prepared such that application at the rate of about 1 to about 200 gallons of solution per acre (about 9 to about 1875 liters per hectare) will provide the required amount of active ingredient. A small amount of nonphytotoxic surfactant typically between 0.05% and 0.5% by weight is usually included to improve the wetting ability of the solution and thus its distribution over the plant surface. Anionic, cationic, nonionic, ampholytic, and zwitterionic surfactants are all useful in this regard.

Suitable anionic surfactants include alkali metal, ammonium, and amine salts of fatty alcohol sulfates having from 8–18 carbon atoms in the fatty chain and sodium salts of alkyl benzene sulfonates having from 9 to 15 carbon atoms in the alkyl chain. Suitable cationic surfactants include dimethyl dialkyl quaternary ammonium halides with alkyl chains of 8 to 18 carbon atoms. Suitable nonionic surfactants include polyoxyethylene adducts of fatty alcohols having 10 to 18 carbon atoms, polyethylene oxide condensates of alkyl phenols with alkyl chains of 6 to 12 carbon atoms and 5 to 25 moles of ethylene oxide condensed onto each mole of alkyl phenol, and polyethylene oxide condensates of sorbitan esters with 10 to 40 moles of ethylene oxide condensed onto each mole of sorbitan ester. Suitable ampholytic surfactants include secondary and tertiary aliphatic amine derivatives with one aliphatic substituent containing 8 to 18 carbon atoms and another containing an anionic water-solubilizing group such as a sulfate or sulfonate. Sodium-3-dodecylaminopropionate and sodium-3-dodecyl amino propane sulfonate are examples. Suitable zwitterionic surfactants include derivatives of aliphatic quaternary ammonium compounds with one aliphatic substituent containing 8 to 18 carbon atoms and another containing an anionic water-solubilizing group. Examples of are 3-(N,N-dimethyl-N-hexadecylammonio)propane-1-sulfonate and 3-(N,N-dimethyl-N-hexadecylammonio)-2-hydroxy propane-1-sulfonate.

C. Emulsifiable Concentrates

Emulsifiable concentrates are solutions in which the active materials and an emulsifying agent are dissolved in a non-watermiscible solvent. Prior to use, the concentrate is diluted with water to form a suspended emulsion of solvent droplets.

Typical solvents for use in emulsifiable concentrates include weed oils, chlorinated hydrocarbons, and non-water-miscible ethers, esters, and ketones.

Typical emulsifying agents are anionic or nonionic surfactants, or mixtures of the two. Examples include long-chain mercaptan polyethoxy alcohols, alkylaryl polyethoxy alcohols, sorbitan fatty acid esters, polyoxyethylene ethers with sorbitan fatty acid esters, polyoxyethylene glycol esters with fatty or rosin acids, fatty alkylol amide condensates, calcium and amine salts of fatty alcohol sulfates, oil-soluble petroleum sulfonates, or preferably mixtures of these emulsifying agents. Such emulsifying agents usually comprise about 1 to 10 weight percent of the total composition.

Typical emulsifiable concentrates contain about 15 to 50 weight percent active material, about 40 to 82 weight percent solvent, and about 1 to 10 weight percent emulsifier. Other additives such as spreading agents and stickers can also be included.

D. Wettable Powders

Wettable powders are water-dispersible compositions containing the active material, an inert solid extender, and one or more surfactants to provide rapid wetting and prevent flocculation when suspended in water.

Suitable solid extenders include both natural minerals and materials derived synthetically from such minerals. Examples include kaolinites, attapulgite clay, montmorillonite clays, synthetic silicas, synthetic magnesium silicate and calcium sulfate dihydrate.

Suitable surfactants include both nonionic and anionic types, and function as wetting agents and dispersants. Usually one of each is included. Preferred wetting agents are alkylbenzene and alkylnaphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, and ditertiary acetylenic glycols. Preferred dispersants are methyl cellulose, polyvinyl alcohol, lignin sulfonates, polymeric alkylnaphthalene sulfonates, sodium naphthalene sulfonate, polymethylene bisnaphthalenesulfonate, and sodium-N-methyl-N(long chain acid) taurates.

Typical wettable powders contain 25 to 90 percent active material, 0.5 to 2.0 percent wetting agent, 0.25 to 5.0 percent dispersant, and from 9.25 to 74.25 weight percent inert extender. Frequently, 0.1 to 1.0 percent of the extender is replaced by a corrosion inhibitor and/or an antifoaming agent.

E. In General

In general, any conventional postemergence method of application can be used, including common equipment such as dusting, spraying, wicking, roll bars, and the like. The amount of active ingredient which is effective in producing the desired result, be it herbicidal or growth-regulating, depends on the nature of the plant species to be controlled and the prevailing conditions. Herbicidal effects are usually achieved at 0.1 to 50 pounds active ingredient per acre, preferably 1 to 10, while plant growth regulation is usually achieved at 0.1 to 20 pounds active ingredient per acre, preferably 0.5 to 5.

What is claimed is:

1. The compound hydroxy stannic tris-N-phosphonomethylglycine.

2. The compound stannic tetra-N-phosphonomethylglycine.

3. A herbicidal composition comprising a herbicidally effective amount of the compound of claim 1 admixed with an inert adjuvant carrier.

4. The method of controlling undesired vegetation comprising adding to the habitat where control is desired a herbicidally effective amount of the compound of claim 1.

5. The method of controlling undesired vegetation comprising adding to the habitat where control is desired a herbicidally effective amount of the composition of claim 3.

6. A herbicidal composition comprising a herbicidally effective amount of the compound of claim 2 admixed with an inert adjuvant carrier.

7. The method of controlling undesired vegetation comprising adding to the habitat where control is desired a herbicidally effective amount of the compound of claim 2.

8. The method of controlling undesired vegetation comprising adding to the habitat where control is desired a herbicidally effective amount of the composition of claim 6.

9. A compound having a ratio of stannic IV cation to N-phosphonomethylglycine anion from about 1:1 to about 1:6.

* * * * *